(12) United States Patent
Xu et al.

(10) Patent No.: US 7,182,937 B2
(45) Date of Patent: Feb. 27, 2007

(54) ANHYDROUS DENTRIFICE FORMULATIONS FOR THE DELIVERY OF INCOMPATIBLE INGREDIENTS

(75) Inventors: Jin Xu, Livingston, NJ (US); Stephen W. Mruphy, Rockaway, NJ (US); Bala Nayar, Dayton, NJ (US); Michael E. Trama, River Vale, NJ (US)

(73) Assignee: Block Drug Company, Inc., Jersey City, NJ (US)

( * ) Notice: Subject to any disclaimer, the term of this patent is extended or adjusted under 35 U.S.C. 154(b) by 279 days.

(21) Appl. No.: 10/398,978

(22) PCT Filed: Oct. 10, 2001

(86) PCT No.: PCT/US01/31742

§ 371 (c)(1),
(2), (4) Date: Jul. 29, 2003

(87) PCT Pub. No.: WO02/30381

PCT Pub. Date: Apr. 18, 2002

(65) Prior Publication Data

US 2004/0047814 A1    Mar. 11, 2004

Related U.S. Application Data

(63) Continuation-in-part of application No. 09/687,784, filed on Oct. 13, 2000, now abandoned.

(51) Int. Cl.
*A61K 8/00* (2006.01)
*A61K 8/18* (2006.01)
*A61Q 11/00* (2006.01)

(52) U.S. Cl. ............... 424/49; 424/48; 424/54; 424/440; 424/667; 424/678; 424/682; 424/719; 433/217.1; 433/228.1

(58) Field of Classification Search ............ None
See application file for complete search history.

(56) References Cited

U.S. PATENT DOCUMENTS

| 3,483,006 | A | * | 12/1969 | Vassilevsky et al. | ........ 106/619 |
| 3,667,978 | A | * | 6/1972 | Vassilevsky et al. | ........ 106/619 |
| 4,612,053 | A | | 9/1986 | Brown et al. | ........... 706/35 |
| RE33,161 | E | | 2/1990 | Brown et al. | ........... 423/308 |
| 5,562,895 | A | | 10/1996 | Tung | ........... 424/57 |
| 5,603,922 | A | | 2/1997 | Winston et al. | ........... 424/49 |
| 5,645,853 | A | * | 7/1997 | Winston et al. | ........... 424/440 |
| 5,817,296 | A | | 10/1998 | Winston et al. | ........... 424/49 |
| 5,866,102 | A | | 2/1999 | Winston et al. | ........... 424/52 |

FOREIGN PATENT DOCUMENTS

| EP | 1 058 535 B1 | 12/2000 |
| WO | WO 01/10392 A2 | 2/2001 |

* cited by examiner

*Primary Examiner*—Frederick Krass
(74) *Attorney, Agent, or Firm*—Nora Stein-Fernandez; Andrea Winslow; Theodore R. Furman

(57) ABSTRACT

A composition for reducing dentinal hypersensitivity and remineralizing exposed dentinal surface and open dentinal tubules, comprising a non-aqueous carrier and a desensitizing amount of a desensitizing/remineralizing agent which consists essentially of a water soluble calcium salt and an incompatible ingredient which would otherwise react with the calcium salt. Upon contact with saliva when applied to an oral cavity, the desensitizing/remineralizing is then formed in situ by the reaction between the calcium salt and the incompatible ingredient, thereby remineralizing exposed dentinal surface and open dentinal tubules.

7 Claims, No Drawings

ANHYDROUS DENTIFRICE FORMULATIONS FOR THE DELIVERY OF INCOMPATIBLE INGREDIENTS

This application a 371 national phase entry application claiming priority from International Application No. PCT/US01/31742, filed Oct. 10, 2001, which is a continuation-in-part of U.S. application Ser. No. 09/687,784, filed Oct. 13, 2000 now abandoned.

FIELD OF THE INVENTION

The invention relates to compositions for the treatment of dentinal hypersensitivity and methods for the treatment of dentinal hypersensitivity using a precipitate forming in situ as the desensitizing/remineralizing agent.

BACKGROUND OF THE INVENTION

Dentinal hypersensitivity is a temporary induced pain sensation produced when hypersensitive teeth are subjected to changes in temperature, pressure or chemical action. Hypersensitivity may occur whenever the dentin or cementum of a tooth is exposed by attrition or abrasion, or when the tooth's finer root surface is exposed by periodontal disease. Dentin generally contains channels, called tubules, that allow material and energy transport between the exterior of the dentin and the interior of the tooth where the nerve is located.

One approach to control dentinal hypersensitivity involves the use of "nerve agents" or "nerve desensitizing agents" in commercial dentifrices comprising strontium ions, fluoride ions, or potassium salts such as potassium bicarbonate, potassium nitrate, potassium chloride, and the like.

Another approach to control dentinal hypersensitivity is to use "tubule blocking agents" to fully or partially occlude tubules. Examples of tubule blocking agents include polystyrene beads, apatite, synthetic or mineral hectorite clay to seal dentinal tubules, polyacrylic acid and water-soluble or water-swellable polyelectrolytes or the salts thereof.

Yet a third approach to control dentinal hypersensitivity is through the mineralization of tubules in dentin thereby counteracting the hyersensitivity problem. U.S. Pat. No. 4,183,915 discloses a one-part stable aqueous solution comprising calcium ions and phosphate ions for the remineralization of dental enamel. The solution also employs an antinucleating agent to maintain the solubility of the calcium phosphate in the presence of fluoride sources. U.S. Pat. No. 4,083,955 discloses a process of remineralizing by consecutive treatment of the tooth surface with separate solutions containing calcium ions and phosphate ions. The fluoride ions may be present in the phosphate solutions. By sequentially and separately applying calcium and phosphate ions, high concentrations of the ions penetrate into the tubules whereby they precipitate as calcium phosphate salts.

U.S. Pat. No. 5,833,957 discloses an improvement with a two-part system in which calcium and phosphate are kept separate, wherein the two compounds when dispensed are mixed and immediately applied to the teeth being treated without the requirement of successive treatments. The two-part system is necessary to prevent the reaction of the calcium, phosphate and/or fluoride salts whereby an insoluble calcium phosphate or hydroxyapatite is formed during storage, leading to the unavailability of calcium ions when the dentifrice is in use. U.S. Pat. No. 5,866,102 offers yet an improved formulation with a water soluble calcium salt, a phosphate salt, and optionally a fluoride-releasing agent. To prevent the reaction of the calcium, phosphate and/or fluoride salts, it is necessary for this system to: a) employ a stabilizing desiccating agent; or b) encapsulate or coat the salts with an oleophilic or polymeric material which prevents a reaction among the active materials.

The inventors have surprisingly formulated dentifrice compositions which control dentinal hypersensitivity through the mineralization of tubules in dentin without the need for stabilizing desiccating agents or coating/encapsulating materials.

SUMMARY OF THE INVENTION

The invention provides a dentifrice composition comprising a desensitizing amount of a desensitizing/remineralizing agent in a non-aqueous carrier, wherein the desensitizing/remineralizing agent consists essentially of a water soluble calcium salt and an incompatible ingredient which would otherwise react with the calcium salt in an aqueous carrier.

The invention further provides a method for desensitizing hypersensitive teeth by applying thereto an oral composition comprising a desensitizing amount of a desensitizing/remineralizing agent in a non-aqueous carrier, wherein the desensitizing/remineralizing agent consists essentially of a water soluble calcium salt and an incompatible ingredient which would otherwise react with the calcium salt in an aqueous carrier.

In one embodiment of the invention, the incompatible ingredient is selected from the group consisting of water-soluble silicates, water-soluble phosphate salts, and water-soluble fluoride salts, or mixtures thereof. In another embodiment, the incompatible ingredient is a water-soluble silicate.

DETAILED DESCRIPTION OF THE INVENTION

By "dentifrice composition," as used herein, means a toothpaste, tooth powder, prophylaxis paste, lozenge, gum, or oral gel.

By the term "desensitizing amount" as used herein, means considering the method of delivery and the formulation, an amount that is sufficient to aid in desensitizing.

By the term "water-soluble," as used herein, means a compound having a property that at least 0.25 gram thereof dissolves in 100 ml of water at 20° C.

The inventors have found that the anhydrous desensitizing composition of the present invention employing a calcium compound and an incompatible ingredient thereof, upon application to the oral cavity with saliva and depending on the incompatible material used, simultaneously forms "desensitizing/remineralizing" agents in situ in the mouth. The resulting "desensitizing/remineralizing" agents include calcium silicate, hydroxyapatite $Ca_{10}(PO_4)_6(OH)_2$, fluoroapatite $Ca_{10}(PO_4)_6F_2$, tricalcium phosphate $Ca_{10}(PO_4)_2$ and various other kinds of known calcium-based compounds that are beneficial for the treatment of hypersensitive teeth and remineralization of tubules. The dentifrice composition of the present invention, without the need for any stabilizing/desiccating/encapsulating/coating materials, surprisingly keeps one or more of the calcium, silicate, phosphate, and/or fluoride salts stable during storage in a closed container prior to application to the oral cavity. The results being sufficient calcium phosphate, calcium silicate, and/or fluoride ions are formed in situ and released to hypersensitive teeth where they are needed the most.

The first component of the desensitizing/remineralizing agent is a water soluble calcium salt for the formation of calcium phosphate (hydroxyapatite), calcium silicate, and the like, that are necessary for the desensitizing/remineralization of the dentin tubules.

Suitable water-soluble calcium compounds include, for example, calcium chloride, calcium nitrate, calcium acetate, calcium citrate, calcium gluconate, calcium benzoate, calcium glycerophasphate, calcium formate, calcium fumarate, calcium lactate, calcium butyrate and calcium isobutyrate, calcium malate, calcium maleate, calcium propionate, calcium valerate or mixtures of water-soluble calcium compounds. In a preferred embodiment, calcium chloride is used.

Concentration of water-soluble calcium compounds are from about 0.05 to 35%. In a preferred embodiment, the concentration is about 2 to 15 wt. %.

The second component of the desensitizing/remineralizing agent of the present invention is one that reacts with the calcium ions to form a precipitate in situ when applied to the oral cavity upon contact with saliva. The second component is selected from the group consisting of alkali metal silicates, water-soluble phosphate salts, fluoride salts, or mixtures thereof.

The second component is present in an amount sufficient to react with the calcium compounds in situ to give an amount effective for desensitizing/remineralizing purposes. Suitably, the second component is present in an amount from about 0.05 to 35 wt. %. In a preferred embodiment, the concentration of the second embodiment is about 1 to 20 wt. %.

Alkali metal silicates include lithium silicate, sodium silicate, potassium silicate, ammonium silicate, and the like. In one embodiment, potassium silicate is used. In another embodiment, the alkali silicate is a mixture of or a mixture of sodium silicate and potassium silicate.

Fluoride sources include sodium fluoride, zinc fluoride, alkali metal difluorophosphates, polyfluorophosphate, and monofluorophosphates such as sodium monofluorophosphate, lithium monofluorophosphate, ammonium monofluorophosphate, aluminum monofluorophosphate, and potassium monofluorophosphate, or mixtures thereof. In one embodiment, the fluoride salt is sodium monofluorophosphate. In another embodiment, sodium fluoride is employed.

The phosphate compounds for use in this invention include alkali metal (e.g., sodium and potassium), ammonium, magnesium, barium and strontium orthophosphates and acid orthophosphates, metaphosphates, pyrophosphates, as well as glycerophosphates, fructose-6-phosphate, sorbitol-6-phosphate, glucose-1-phosphate, glucose-6-phosphate, and the like. Mixtures of such phosphate sources with each other or with calcium phosphate may be employed. If desired, a water-soluble salt yielding both calcium and phosphate ion, such as tricalcium phosphate and monobasic-calcium orthophosphate can also be employed. In one embodiment, the phosphate compound is disodium hydrogen phosphate.

The inventors have surprisingly found that the first component calcium salts, without the need for a desiccating agent or encapsulating agent to keep separate from the phosphate salts, co-exist with the phosphate salts in storage and are available for reaction in situ upon contact with saliva in the mouth, thus forming calcium phosphate based compounds, in particular hydroxyapatite represented by $Ca_{10}(PO_4)_6(OH)_2$. In addition to the hydroxyapatite already mentioned, fluoroapatite $Ca_{10}(PO_4)_6F_2$, tricalcium phosphate $Ca_{10}(PO4)2$ and various other kinds of known calcium phosphate-based compounds can be formed depending on the types of "incompatible ingredients" used as the second component for the formation of the desensitizing/remineralizing agent.

Optional anti-hypersensitivity agents or nerve desensitizing agents commonly used in the dentifrice art, i.e., agents that are neuroactive, ions or salts which have a pain reducing or analgesic activity, may also be included in the composition of the present invention. Examples of nerve agents include, but not limited to, potassium or strontium salts, including potassium bicarbonate, potassium citrate, potassium chloride, potassium nitrate, strontium chloride, strontium acetate, strontium nitrate, and potassium or strontium salts of other similar conjugate acids, and mixtures thereof.

Ingredients typically included in oral health care compositions may be used in the compositions in accordance with the invention including abrasive polishing materials, sudsing agents, flavoring agents, humectants, binders, sweetening agents, and the like. Abrasives which may optionally be used in the compositions of the invention include alumina and hydrates thereof, such as alpha alumina trihydrate, magnesium carbonate, calcined aluminum silicate and aluminum silicate, calcium carbonate, zirconium silicate, polymethylmethacrylate, powdered polyethylene, silica xerogels, hydrogels and aerogels, and the like. Depending on the form that the dentifrice composition is to take and whether the substrate is an abrasive-based material, the abrasive may be present in an amount of from 0 to 50% by weight.

The anhydrous carrier for the dentifrice composition of the present invention is a single, or a combination of, water-free organic solvents including mineral oils, glycerol, polyol, sorbitol, polyethylene glycol, propylene glycol, copolymers of ethylene oxide and propylene oxide, petrolatum, triacetin, and the like. The carrier is present in an amount of about 10 to 90% by weight for toothpastes.

Binders suitable for use in the compositions of the invention include hydroxyethyl cellulose, and hydroxypropyl cellulose, as well as xanthan gums, Iris moss and gum tragacanth. Binders may be present in the amount from 0.01 to 20%.

Sweeteners suitable for use may be present at levels of about 0.1% to 10% and include saccharin and xylitol.

Optional fluoride sources commonly used in oral health care compositions such as sodium fluoride, stannous fluoride, sodium monofluorophosphate, zinc ammonium fluoride, tin ammonium fluoride, calcium fluoride and cobalt ammonium fluoride may be included for delivering anti-caries benefit. Fluoride ions are typically provided at a level of from 0 to 1500 ppm, preferably 50 to 1500 ppm, although higher levels up to about 3000 ppm may be used.

Surfactants, such as a soap, anionic, nonionic, cationic, amphoteric and/or zwitterionic, may be present within the range of 0 to 15%, preferably 0.1 to 15%, more preferably 0.25 to 10% by weight. Anionic and/or nonionic surfactants are most preferred, and include for example, sodium lauryl sulfate, sodium lauroyl sarcosinate and sodium dodecylbenzene sulfonate. Flavors are usually included in low amounts, such as from 0.01 to about 5% by weight, especially from 0.1% to 5%.

Antibacterial agents include for example phenolics and salicylamides, and sources of certain metal ions such as zinc, copper, silver and stannous (e.g., zinc, copper and stannous chloride, and silver nitrate) may also be, and preferably are, included.

Dyes/colorants suitable for oral health care compositions, i.e. FD & C Blue #1, FD & C Yellow #10, FD & C Red #40, etc., may be employed. Various other optional ingredients may be included in the compositions of the invention such as preservatives, vitamins such as vitamin C and E, other anti-plaque agents such as stannous salts, copper salts, strontium salts and magnesium salts. Also included may be pH adjusting agents; anti-caries agents such as calcium glycerophosphate, sodium trimetaphosphate; anti-staining compounds such as silicone polymers, plant extracts and mixtures thereof. Additionally, polymers, particularly anionic polymers, such as polycarboxylates or polysulfonates, or polymers containing both a carboxylate and a sulfonate moiety, phosphonate polymers or polyphosphates may be included.

The dentifrice compositions of the present invention are typically in the form of toothpastes or dentifrices to be brushed on the teeth. However, other delivery systems may also be used including tooth powder, mouthwash, lozenge, buccal adhesive patch, oral spray, coatings or chewing gum, and the like.

The composition of this invention are prepared by conventional methods of making oral health care formulations by mixing the ingredients in an order that is convenient to achieve the desired effects. For instance, forming a gel with gelling agents and then adding other ingredients in toothpaste and gel dentifrice embodiments.

In dentifrice form, the composition may be packaged in a conventional plastic laminate or metal tube or a dispenser. It may be applied to dental surfaces by any physical means, such as a toothbrush, fingertip or by an applicator directly to the sensitive area. Solid dosage forms examples include pastilles, lozenges, chewing gums, tablets, mouthstrips, balms, and the like.

EXAMPLES

The instant invention will be exemplified by the following non-limiting examples. In all examples, all temperatures are in degrees centigrade and all parts and percentages are by weight, unless otherwise indicated.

In Examples 1–3, all ingredients except for the flavor and synthetic amorphous silica are mixed together under mechanical agitation until well-mixed. The amorphous silica is then added and the mixing continues under vacuum for 5 minutes. Lastly, flavor is added and the mixing continues for another 10 minutes under vacuum.

TABLE 1

| Ingredients in wt. % | Example 1 | Example 2 | Example 3 |
| --- | --- | --- | --- |
| Flavor | 1.000 | 1.000 | 1.000 |
| Glycerin | 48.000 | 48.000 | 42.000 |
| PEG 600 | 13.366 | 13.366 | 13.366 |
| Precipitated silica | 9.000 | — | — |
| PEG 3350 | 2.500 | 2.500 | 2.500 |
| Potassium Nitrate | 5.000 | 5.000 | 5.000 |
| Sodium monofluorophosphate | 0.834 | 0.834 | 0.834 |
| Sodium saccharin USP | 0.300 | 0.300 | 0.300 |
| Titanium dioxide USP | 0.500 | 0.500 | 0.500 |
| Potassium silicate | — | 14.500 | 14.500 |
| Calcium nitrate tetrahydrate | — | — | 9.500 |
| Disodium hydrogen phosphate | 5.000 | — | — |
| Calcium chloride | 1.500 | 4.500 | — |
| Sodium Lauryl Sulfate | 3.000 | 1.500 | 1.500 |
| Citric Acid | 5.000 | 3.000 | — |
| Synthetic Amorphous Precipitated silica | 5.000 | 5.000 | 9.000 |

In vitro tests demonstrating desensitizing effect. The formulations from Examples 1–3 were tested using the method described by Pashley, (J. Periodontology, vol. 55, no. 9, p. 522, September 1994), which is also described in U.S. Pat. No. 5,270,031. In this method, intact human molars free from caries and restorations are sectioned perpendicularly to the long axis of the tooth with a metallurgical saw into thin sections of about 0.4 to about 0.6 mm thick. Sections containing dentin and free of enamel are obtained for testing and are then etched with an ethylenediamine tetraacetic acid solution to remove the smear layer. The disc is mounted into the split-chambered device described by Pashley which is a special leak-proof chamber connected to a pressurized fluid reservoir containing a tissue culture fluid. By using a mixture of pressurized nitrogen and carbon dioxide gas, the fluid can be made at physiological pH. To further ensure accuracy, the discs are wetted with human saliva to approximate the intra-oral condition. The apparatus includes a gas capillary tube mounted on a ruler or other measuring instrument and an air bubble as a function of time, with which fluid flow through the dentin disc can be measured.

Following measurement of the baseline fluid flow in the dentin disc, an experimental dentifrice is applied to the external surface with a nylon brush. After a defined period of brushing, the experimental material is rinsed off, and the post-application hydraulic conductance is measured. In addition, measurements on the same disc are taken after an excessive back pressure (in terms of physiological conditions) is applied. This is used as a measure of the tenacity of the plug. In this fashion, the ability of various experimental materials both alone and as components of dentifrice systems can be tested for their ability to obstruct fluid flow in the dentinal tubules. In tests comparing the percent flow reduction induced by brushing the dentifrice formulations of Examples 1–3 with placebo dentifrices (without the desensitizing/remineralizing agent formed in situ of the present invention), it was found that the percent flow reduction of the compositions of the present invention range between 80–100%, and the percent flow reduction for the placebo dentifrices was in the range of 0–30%.

Test Demonstrating Stability Effect. Analytical tests on Examples 1–3 measuring the amount of sodium monofluorophosphate before and after formulation showed that the sodium monoflourophosphate is stable in the formulations of the present invention, i.e., no measurable reduction in the amount added to the formulation and no measurable reaction with the incompatible calcium compounds, thus leaving the calcium ions and the fluoride ions free for the protection of the teeth against decay and hypersensitivity.

What is claimed is:

1. A composition that is a toothpaste, a tooth powder, a prophylaxis paste, a lozenge, a gum or an oral gel, for reducing dentinal hypersensitivity and remineralizing exposed dentinal surface and open dentinal tubules, comprising a desensitizing amount of a desensitizing/remineralizing agent in a non-aqueous carrier which is formed in situ upon contact with saliva when applied to an oral cavity,
   wherein said desensitizing/remineralizing agent consists essentially of a water soluble calcium salt and a water soluble silicate selected from lithium silicate, sodium silicate, potassium silicate or ammonium silicate, or mixtures thereof, which would otherwise react with the calcium salt in an aqueous carrier, and
   wherein said calcium salt reacts with said water soluble silicate upon contact with the saliva forming said desensitizing/remineralizing agent in situ for remineralizing exposed dentinal surface and open dentinal tubules.

2. The composition of claim 1, further comprising a desensitizing agent selected from the group consisting of potassium bicarbonate, potassium citrate, potassium chloride, potassium nitrate, strontium chloride, strontium acetate, strontium nitrate, or mixtures thereof.

3. The composition of claim 1, wherein said water soluble calcium salt is present in an amount of from about 0.05 to 35 wt. %, and said water soluble silicate for reaction with said water soluble calcium salt in situ is present in an amount of from about 0.05 to 35 wt. %.

4. The composition of claim 3, wherein said water soluble calcium salt is present in an amount of from about 2 to 15 wt. %, and said water soluble silicate for reacting with said water soluble calcium salt in situ forming a desensitizing/remineralizing agent is present in an amount of from about 1 to 20 wt. %.

5. A method for reducing dentinal hypersensitivity and remineralizing exposed dentinal surface and open dentinal tubules in a tooth comprising the steps of administering to the tooth a composition comprising a desensitizing amount of a desensitizing/remineralizing agent in a non-aqueous carrier, said desensitizing/remineralizing agent is formed in situ upon contact with saliva end the tooth, wherein said desensitizing/remineralizing agent consists essentially of a water soluble calcium salt and a water soluble silicate selected from lithium silicate, sodium silicate, potassium silicate, or ammonium silicate or a mixture thereof which would otherwise react with the calcium salt, and wherein said calcium salt reacts with said water soluble silicate upon contact with saliva and the tooth forming said desensitizing/remineralizing agent in situ for remineralizing exposed dentinal surface and open dentinal tubules in the tooth.

6. The method of claim 5, wherein said water soluble calcium salt is present in an amount of from about 0.05 to 35 wt. %, and said water soluble silicate —for reaction with said water soluble calcium salt in situ is present in an amount of from about 0.05 to 35 wt. %.

7. The method of claim 5, wherein said composition further comprises a desensitizing agent selected from the group consisting of potassium bicarbonate, potassium citrate, potassium chloride, potassium nitrate, strontium chloride, strontium acetate, strontium nitrate, or mixtures thereof.

* * * * *